(12) United States Patent  (10) Patent No.: US 7,938,580 B2
Gaskell et al.  (45) Date of Patent: May 10, 2011

(54) STERILIZABLE PACKAGE WITH A HIGH BARRIER TO OXYGEN

(75) Inventors: Paul Gaskell, Newtownabbey (GB); Conor Brendan Ward, Derry (GB); Gerry A. King, Derry (GB)

(73) Assignee: Perfecseal, Inc., Oshkosh, WI (US)

( * ) Notice: Subject to any disclaimer, the term of this patent is extended or adjusted under 35 U.S.C. 154(b) by 679 days.

(21) Appl. No.: 11/667,719

(22) PCT Filed: Dec. 7, 2005
(Under 37 CFR 1.47)

(86) PCT No.: PCT/US2005/044261
§ 371 (c)(1),
(2), (4) Date: Mar. 24, 2008

(87) PCT Pub. No.: WO2006/063050
PCT Pub. Date: Jun. 15, 2006

(65) Prior Publication Data
US 2009/0166237 A1  Jul. 2, 2009

(30) Foreign Application Priority Data
Dec. 8, 2004  (IE) .................................. S2004/0826

(51) Int. Cl.
*B65D 30/22* (2006.01)
*B65D 33/01* (2006.01)
*B65D 30/08* (2006.01)
*B65D 73/00* (2006.01)
*A61B 17/06* (2006.01)
*B65B 55/02* (2006.01)

(52) U.S. Cl. .......... 383/38; 383/102; 383/109; 383/113; 206/439; 206/484.1; 53/425

(58) Field of Classification Search ................... 383/38, 383/102, 109, 113; 206/439, 484.1, 484.2; 53/425
See application file for complete search history.

(56) References Cited

U.S. PATENT DOCUMENTS
2,595,708 A  5/1952 Salfisberg
3,754,700 A  8/1973 Bonk
(Continued)

FOREIGN PATENT DOCUMENTS
EP  0 603 789 B1  4/2004
(Continued)

*Primary Examiner* — Jes F Pascua
(74) *Attorney, Agent, or Firm* — Cedric M. Richeson; Christine E. Parsons

(57) ABSTRACT

A package (599) with three layers allows sterilization of the package contents, provides a separate area for a scavenger and minimizes the oxygen transmission rate for the package and has, in one embodiment, a third layer (330) with a first section (336) of breathable polymeric material, a second section (334) of substantially non-breathable polymeric material and a third section (332) of breathable polymeric material which is positioned between a first layer (512) of substantially non-breathable polymeric material and a second layer (514) of substantially non-breathable polymeric material. The first layer (512) and the second layer (514) are fixed together to define a non-breathable pouch (516); and the third layer (330) is fixed to the first layer (512) and the second layer (514) and divides the non-breathable pouch (516) into a first compartment (592) and a second compartment (594). The outer seal (518) fixing the first layer (512) to the second layer (514) does not include any interposing first section (336) of the third layer (330).

64 Claims, 8 Drawing Sheets

U.S. PATENT DOCUMENTS

| | | |
|---|---|---|
| 3,819,106 A | 6/1974 | Schuster |
| 3,939,971 A | 2/1976 | Tulis |
| 4,203,520 A | 5/1980 | Schuster |
| 4,270,658 A | 6/1981 | Schuster |
| 4,367,816 A | 1/1983 | Wilkes |
| 4,482,053 A | 11/1984 | Alpern et al. |
| 4,603,538 A | 8/1986 | Shave |
| 4,660,721 A | 4/1987 | Mykleby |
| 4,714,595 A | 12/1987 | Anthony et al. |
| 4,730,726 A | 3/1988 | Holzwarth |
| 4,744,673 A | 5/1988 | Nakamura |
| 5,102,234 A | 4/1992 | Levy |
| 5,222,600 A | 6/1993 | Stoddard et al. |
| 5,241,149 A | 8/1993 | Watanabe et al. |
| 5,392,590 A | 2/1995 | Ambrose et al. |
| 5,590,778 A | 1/1997 | Dutchik |
| 5,683,795 A | 11/1997 | Ambrose et al. |
| 5,715,943 A | 2/1998 | Thompson, Jr. |
| 5,816,403 A | 10/1998 | Wilkes et al. |
| 5,947,288 A | 9/1999 | Dykstra et al. |
| 6,059,112 A | 5/2000 | Dykstra et al. |
| 6,065,597 A | 5/2000 | Pettersson et al. |
| 6,189,694 B1 * | 2/2001 | Weiss et al. ............ 206/484.1 |
| 6,530,477 B1 * | 3/2003 | Martorano et al. ........ 206/524.2 |
| 6,540,401 B2 * | 4/2003 | Allan ............................ 383/107 |
| 6,554,887 B1 | 4/2003 | Inglis |
| 7,631,760 B2 * | 12/2009 | Guelzow et al. ............... 206/438 |
| 2002/0108877 A1 * | 8/2002 | Allan ............................. 206/439 |
| 2004/0187438 A1 | 9/2004 | Clarke et al. |
| 2005/0067312 A1 | 3/2005 | Gupta et al. |
| 2005/0069452 A1 | 3/2005 | Varma et al. |

FOREIGN PATENT DOCUMENTS

| | | |
|---|---|---|
| EP | 0 846 445 B1 | 7/2004 |
| IE | S2003/0044 | 11/2004 |
| WO | WO 2004/039419 A1 | 5/2004 |
| WO | WO 2004/066876 A1 | 8/2004 |
| WO | WO 2004/071308 A1 | 8/2004 |

\* cited by examiner

STERILIZABLE PACKAGE WITH A HIGH BARRIER TO OXYGEN

BACKGROUND OF THE INVENTION

The present invention relates to packaging and, more particularly, to packaging that allows sterilization of its contents with a subsequent high barrier to the ingress of oxygen and water vapor.

Many items, including, but not limited to, medical items such as drug-eluting stents, are required to be sterilized while in a package and, after sterilization, are required to be substantially isolated from oxygen and water vapor for prolonged time periods. To allow sterilization of an item in a package, the package may be formed from a breathable material that allows sterilizing gas to pass through the breathable material. These breathable materials include spun-bonded olefin products such as those sold by E.I. Du Pont de Nemours and Company (Wilmington, Del.) under the trademark TYVEK®. After sterilization and for the remainder of the life of the package, the breathable material provides a tortuous path for microbes, bacteria and other contaminants, allowing the package and its contents to remain sterile for a prolonged time period.

The breathable material, however, does not act as a barrier to the ingress of gases, including, but not limited to, oxygen, or water vapor. To provide a barrier, the packaging may be formed from a foil or other high-barrier material; however, high-barrier material does not allow sterilizing gas to pass through the material into the package.

Additionally, some packages require some type of scavenger to remove gases, moisture, etc. This scavenger cannot be exposed to sterilizing gas and must be added to the package after sterilization. As it is added after sterilization, the scavenger is not sterile and, therefore, must not have direct contact with the sterile contents.

U.S. Pat. No. 5,947,288 (Dykstra, et. al.) and U.S. Pat. No. 6,059,112 (Dykstra, et. al.) disclose a sterilizable pouch package with three layers wherein the inner layer has a perforation line and is of like length to, but narrower width than, the outer layers; the side edges of the inner layer are preferably unsealed in order to facilitate sterile presentation of the sterilized contents of the package.

U.S. Pat. No. 5,241,149 (Watanabe, et. al.) discloses a three-layer package in bag-form wherein an inner air-permeable film is sealed to the side edges of the package along with outer air-impermeable layers.

U.S. Patent Application 2005/0069452 (Varma, et. al.), PCT Application WO 2004/066876 (Clarke, et. al.) and Short-Term Irish Patent S83657 (Clark, et. al.) disclose a package for a drug-eluting stent. This package has two compartments separated by a breathable membrane internal wall wherein the side edges of the breathable membrane internal wall are included in the outer walls of the package.

PCT Application 2004/071308 (Duffy) discloses a three-layer pouch wherein the three layers are assembled and sealed together simultaneously by sandwiching an internal gas permeable microbe impermeable partition between two outer layers of material.

Prior art sterilizable packaging typically comprised a pouch with one foil layer and one TYVEK® layer, a thermoform tray insert in a foil pouch, or a thermoform tray with a TYVEK® lid in foil pouch. Such conventional packaging does not provide for regulation of ambient conditions such as circulation of air, exposure to oxygen or absorption of gases, moisture, etc. Without such regulation, the efficacy of the packaging and its contents may be compromised.

Accordingly, there is a need for a package that allows sterilization of its contents, provides for a separate area for a scavenger and minimizes the oxygen and water vapor transmission rates.

BRIEF SUMMARY OF THE INVENTION

The present invention provides a package with at least three layers. One layer with at least one section of breathable polymeric material and at least one section of substantially non-breathable polymeric material is positioned between two layers of substantially non-breathable polymeric material. The two layers of non-breathable material are fixed together to define a non-breathable pouch. The layer with the breathable and non-breathable sections is fixed to the layers of non-breathable material and divides the non-breathable pouch into two compartments. The outer seal fixing together the two layers of non-breathable material does not include a section of breathable material from the layer with the breathable and non-breathable sections.

The layer with the breathable and non-breathable sections must have at least one section of non-breathable material and at least one section of breathable material and optionally may include two or more sections of breathable material. For example, when two sections of breathable material are present, the section of non-breathable material may be positioned between and connect the two sections of breathable material. The breathable section or sections need not necessarily extend across the whole width of this layer and may alternatively form, for example, one or more patches or windows in this layer.

The three layers comprising the package may have different lengths, and the layer with the breathable and non-breathable sections may have a width less than the layers of non-breathable material. The two compartments formed by the three layers may be individually sealed via hermetic closing seals, and the closing seal of the second compartment includes only sections of the non-breathable material from the layer with the breathable and non-breathable sections. Such a seal minimizes the oxygen transmission rate for the package.

The package described herein may also be used in a method of packaging an item. This method of packaging an item may include providing a package as that described herein, placing an item in the first compartment of that package, sealing the first compartment, introducing a sterilizing gas into the first compartment, removing the sterilizing gas from the package, placing another item in the second compartment, and sealing the second compartment to provide a hermetically sealed package

DETAILED DESCRIPTION OF THE INVENTION

The present invention relates to a package for sterilizable devices, such as medical devices, particularly drug-eluting stents. This package includes two compartments: a compartment for receiving and sterilizing one or more devices and a compartment for receiving a second item, such as a gas scavenger and/or a desiccant. This package may be a flexible package but is not limited to a flexible package. The attached figures disclose some, but not all, embodiments of this package and are further discussed herein. A key feature of the present invention is the provision of hermetic seals having a high barrier to the transfer of oxygen across the seal edges in combination with the sterilizable compartmental structure as claimed.

Figure 1:
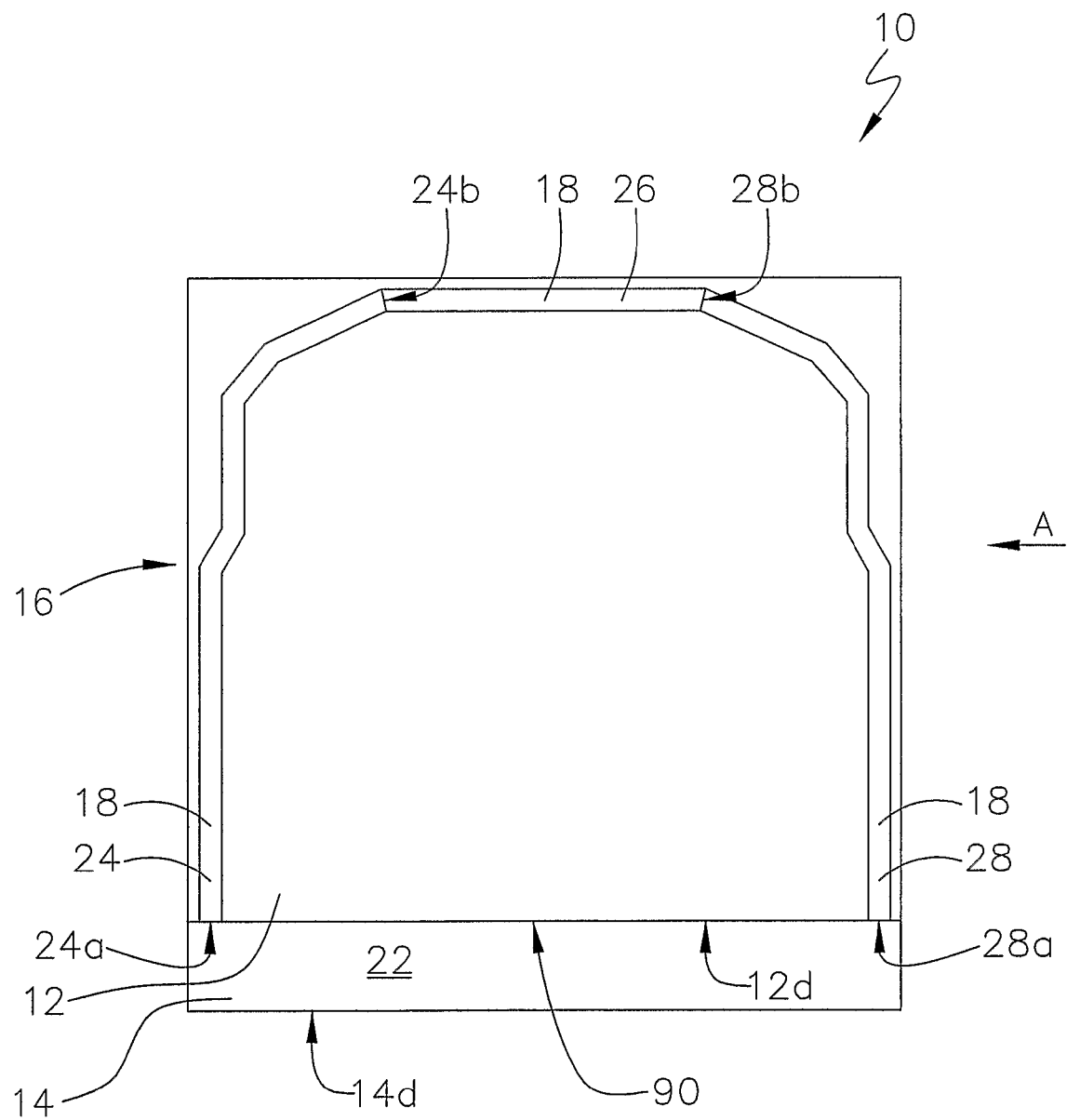
FIG. 1 is a plan view of a first component of the package described herein.

Referring now to the drawings, FIG. 1 is a plan view of a first component 10 of the inventive package described herein. The dimensions in all drawings are for illustration purposes only and are not necessarily to scale. The component 10 comprises a first layer 12 and a second layer 14 fixed together by an outer peripheral seal 18 to form a non-breathable pouch 16. The first layer 12 and the second layer 14 comprise non-breathable polymeric material. The first layer 12 and the second layer 14 may be formed from two individual sheets or formed from one continuous sheet folded to form the first layer 12 and the second layer 14. When the first layer 12 and the second layer 14 are formed from two individual sheets, the outer seal 18 is continuous around the periphery of the package and comprises a first continuous portion 24 having a first end 24a and a second end 24b, an opposing second continuous portion 28 having a first end 28a and a second end 28b and a top continuous portion 26. The top continuous portion 26 is connected to the first portion 24 at the second end 24b of the first portion 24 and is connected to the second portion 28 at the second end 28b of the second portion. When the first layer 12 and the second layer 14 are formed from one continuous sheet, the outer seal 18 comprises the first portion 24 and the second portion 28, and a folded edge 13 (see FIG. 6F) replaces the top portion 26.

The pouch 16 has an opening 90 formed by the first layer bottom edge 12d, the second layer bottom edge 14d and the first ends 24a, 28a of the first portion 24 and the second portion 28, respectively, of the outer seal 18. In the embodiment depicted in FIG. 1, the first layer 12 and the second layer 14 are generally rectangular, and the second layer 14 has a length greater than the first layer 12 so that a portion 22 of the second layer 14 projects beyond the first layer bottom edge 12d. However, the first layer 12 and the second layer 14 are not limited to rectangular shape and may be of different shapes, including, but not limited to, square, circle or oval. Also, the second layer 14 is not limited to having a length greater than the first layer 12. The first layer 12 and the second layer 14 may be of the same length, or the first layer 12 may have a length greater than the second layer 14. As used herein, the term "length" is defined as the axis including the openings or mouths of the package. Advantageously, the length of the pouch 16 may be from about 18.5 cm to about 56.5 cm, and the width of the pouch 16 may be from about 13.5 cm to about 41.5 cm. However, the length and the width are not limited to these dimensions. Greater and lesser dimensions are contemplated, and suitable minimum dimensions are a function of the item to be packaged.

Figure 6A:
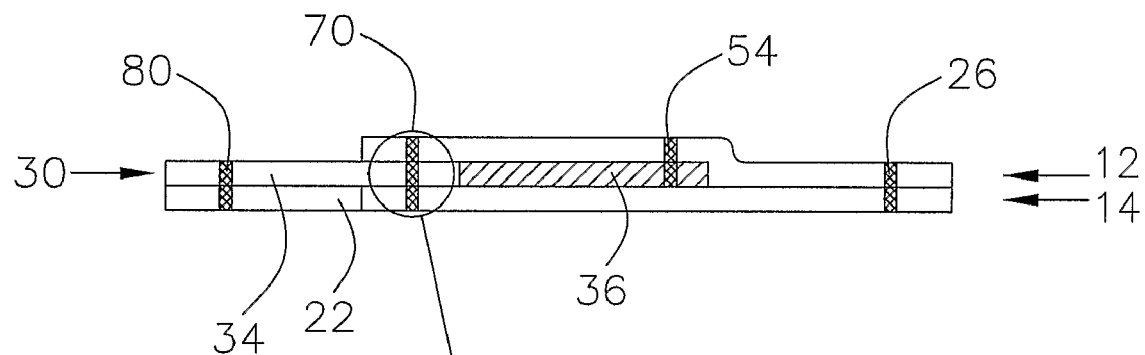
FIG. 6A is a cross-sectional side view of FIG. 4
Figure 6B:
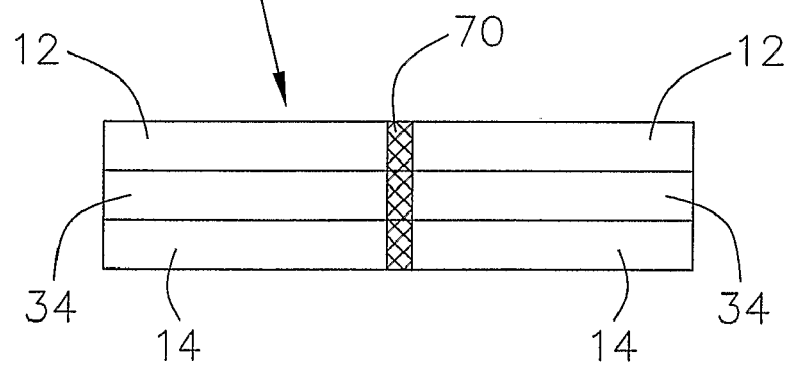
FIG. 6B is an enlarged view of part of the view of FIG. 6A
Figure 6C:
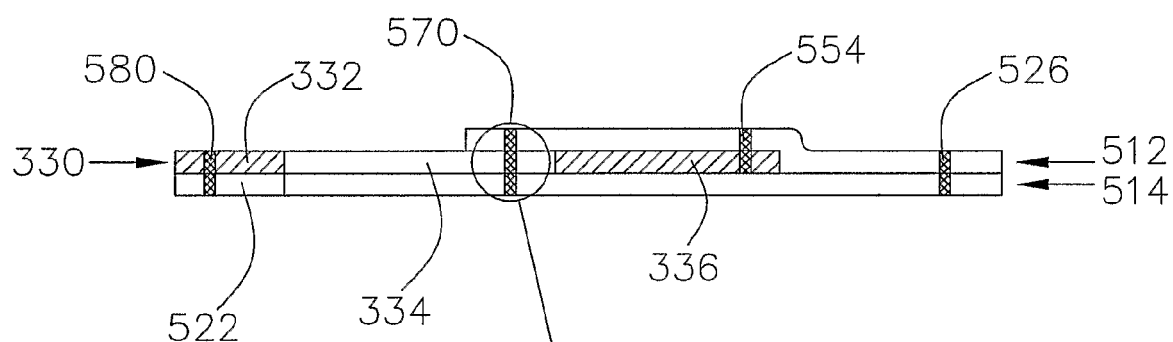
FIG. 6C is a cross-sectional side view of FIG. 5.
Figure 6D:
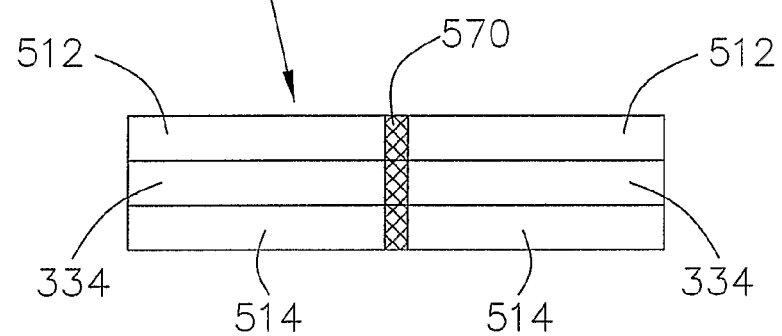
FIG. 6D is an enlarged view of part of the view of FIG. 6A.
Figure 6E:
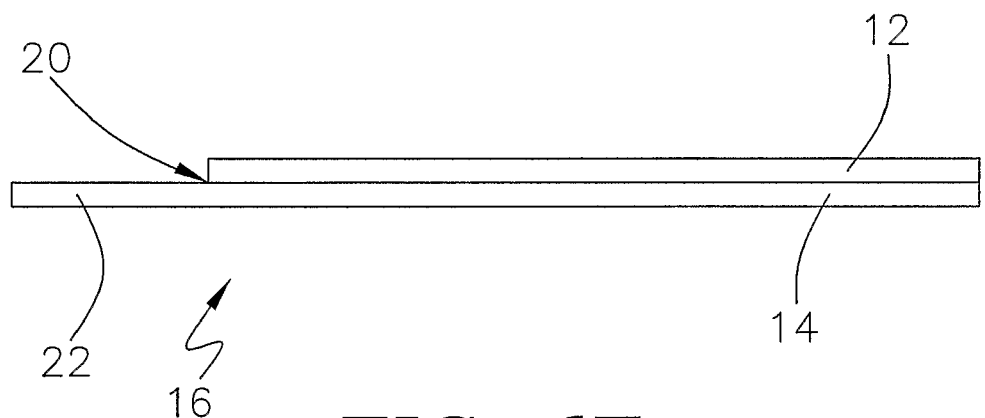
FIG. 6E is a side view of a first embodiment of FIG. 1.
Figure 6F:
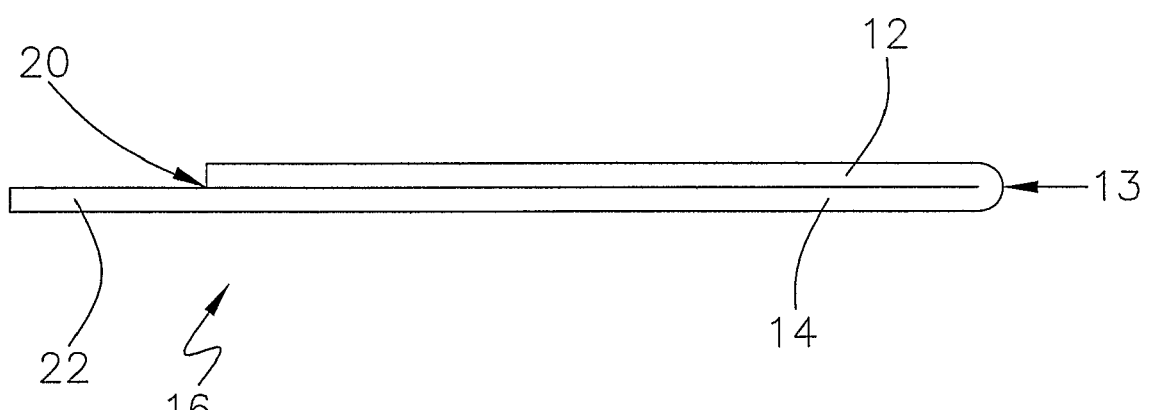
FIG. 6F is a side view of a second embodiment of FIG. 1.

Referring now to FIG. 6E and FIG. 6F, side views of alternative embodiments of the pouch 16 are depicted. FIG. 6E is a side view of a first embodiment of the pouch 16 in FIG. 1, from the direction indicated by arrow A in FIG. 1. In FIG. 6E, the first layer 12 and the second layer 14 are formed from two individual sheets. FIG. 6F is a side view of a second embodiment of the pouch 16 in FIG. 1, again from the direction indicated by arrow A in FIG. 1. In FIG. 6F, the first layer 12 and the second layer 14 are formed from one continuous sheet folded to form the first layer 12 and the second layer 14 joined in a folded edge 13. In either the embodiment of FIG. 6E or the embodiment of FIG. 6F, the first layer 12 and the second layer 14 may each have a total thickness from about 50 to about 150 microns. However, the thicknesses are not limited to these dimensions. Greater and lesser dimensions are contemplated.

Figure 2A:
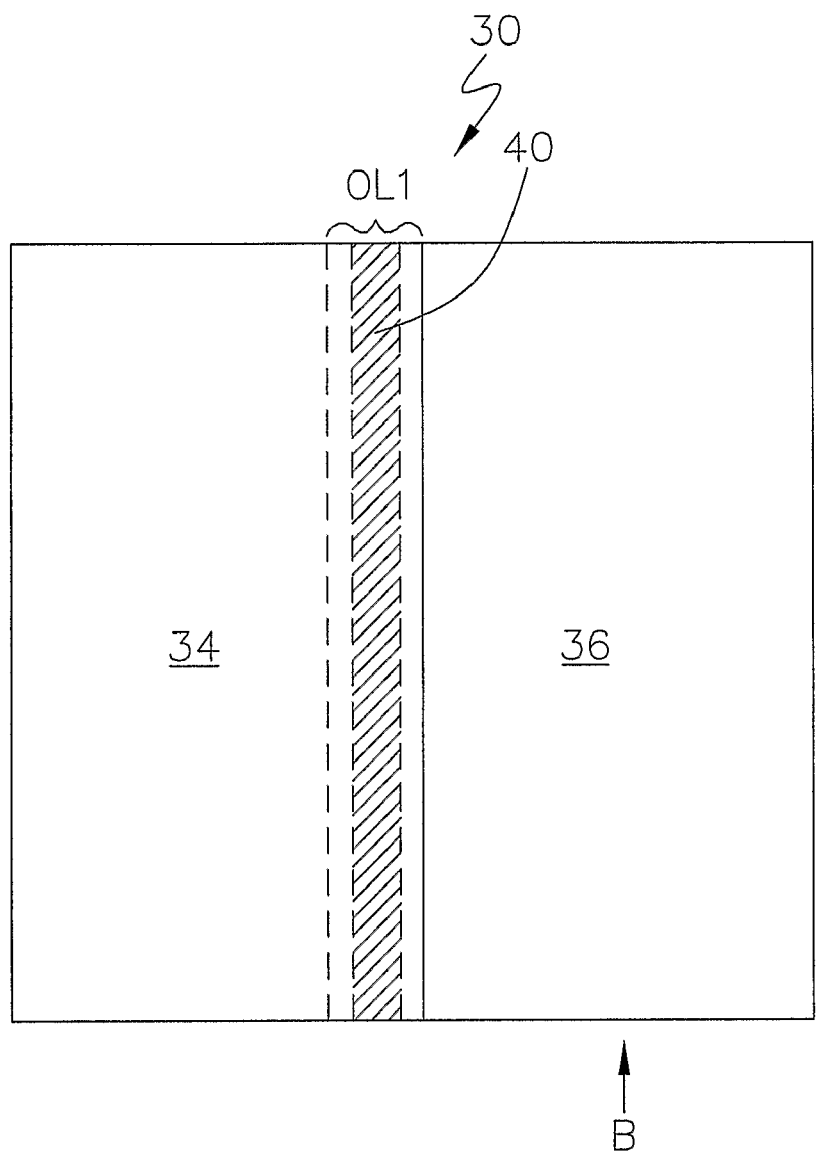
FIG. 2A is a plan view of a first embodiment of a second component of the package described herein.
Figure 2B:
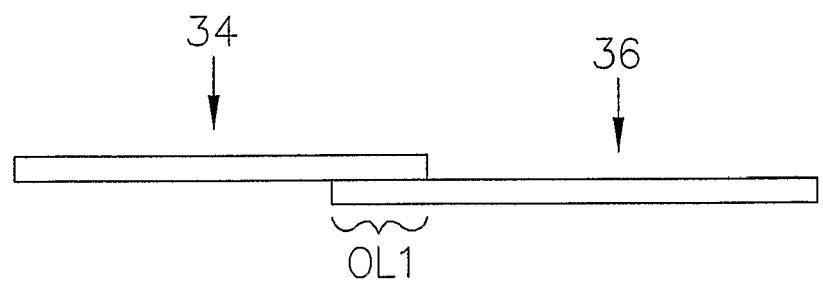
FIG. 2B is a side view of FIG. 2A.

Referring now to FIG. 2A, a plan view is depicted of a first embodiment of a second component of the package described herein. This second component is a third layer 30. In this first embodiment, the third layer 30 comprises a first section 36 and a second section 34. The sections are arranged side-by-side in a co-planar manner. The first section 36 overlaps the second section 34 at OL1. The first section 36 and the second section 34 are fixed together at OL1 by a first overlap seal 40. Other means of fixing together the first section 36 and the second section 34 (as well as optional additional sections) include, but are not limited to, butt seals and sealing tape. The first section 36 comprises breathable polymeric material, and the second section 34 comprises non-breathable polymeric material FIG. 2B is a side view of this first embodiment of the third layer 30, from the direction indicated by arrow B in FIG. 2A. This third layer 30 may have a total thickness from about 75 microns to about 225 microns. However, the thickness is not limited to these dimensions. Greater and lesser dimensions are contemplated.

Figure 3A:
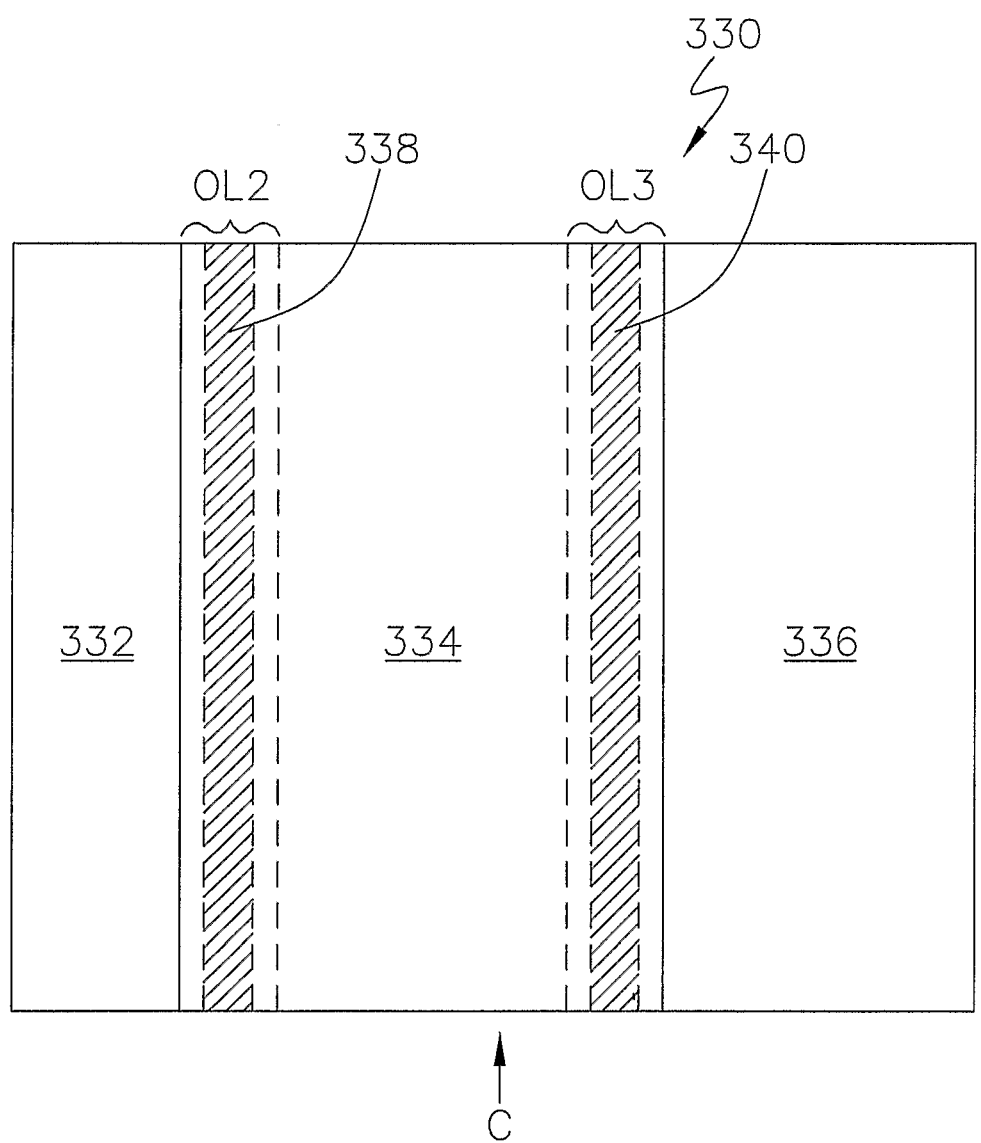
FIG. 3A is a plan view of a second embodiment of the second component of the package described herein.

FIG. 3A is a plan view of a second embodiment of the third layer. This second embodiment of the third layer 330 is similar to the first embodiment depicted in FIG. 2A and FIG. 2B but further comprises a third section 332. In this second embodiment, the first section 336, the second section 334 and the third section 332 are arranged side-by-side in a co-planar manner with the second section 334 positioned between and connecting the first section 336 and the third section 332. The second section 334 overlaps both the first section 336 and the third section 332 along opposite sides, at OL3 and OL2, respectively. The first section 336 and the second section 334 are fixed together at OL3 by the first overlap seal 340, and the second section 334 and the third section 332 are fixed together at OL2 by a second overlap seal 338. The first section 336 comprises breathable polymeric material, the second section 334 comprises non-breathable polymeric material, and the third section 332 comprises breathable polymeric material.

Figure 3B:
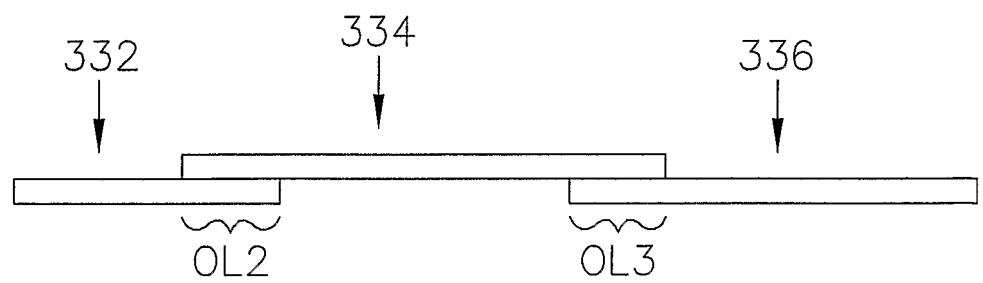
FIG. 3B is a side view of FIG. 3A.

FIG. 3B is a side view of this second embodiment of the third layer 330, from the direction indicated by arrow C in FIG. 3A. This third layer 330 may have a total thickness from about 75 microns to about 225 microns. However, the thickness is not limited to these dimensions. Greater and lesser dimensions are contemplated.

Various materials may be used for the three layers and the sections thereof. Gurley Hill porosity values may be used to select the materials. "Gurley Hill porosity" refers to the air resistance of an approximately 6.45 cm$^2$ (1 in$^2$) circular area of test sample using a pressure differential of 1.22 kPa and is measured in accordance with International Standard ISO 5636-5, "Paper and board—Determination of air permeance and air resistance (medium range)—Part 5: Gurley method." Gurley Hill porosity values are reported in the amount of time (seconds) required for 100 cm³ of air to pass through the test sample. In general, Gurley Hill porosity values indicate the gas barrier strength of a sample; lower values indicate the sample is more porous. Samples with Gurley Hill porosity values greater than 100 seconds are generally considered substantially non-breathable. Accordingly, for the package described herein, the first layers 12, 512, the second layers 14, 514, the second section 34 of the third layer 30 and the second section 334 of the third layer 330 may each have a Gurley Hill porosity value greater than 100 seconds. The first section 36 of the third layer 30, the first section 336 of the third layer 330 and the third section 332 of the third layer 330 may each have a Gurley Hill porosity value less than 100 seconds, preferably less than 80 seconds and more preferably less than 50 seconds.

Specific materials that may be used for the first layers 12, 512, the second layer 14, 514, the second section 34 of the third layer 30 and the second section 334 of the third layer 330 include heat sealable polymers such as polyolefins, polyethylene terephthalates, nylons, ethylene homopolymers or copolymers, or mixtures thereof in any number of lamina, particularly, but not limited to, one lamina to nine laminae. The ethylene homopolymers or copolymers may include high density polyethylene homopolymers, high density polyethylene copolymers of ethylene and alpha olefins (such as 1-butene or 1-hexene), ultra high molecular weight polyethylene, low density polyethylene homopolymers, low density polyethylene copolymers of ethylene and polar groups (such as vinyl acetate or ethyl acrylate), linear low density polyethylene copolymers of ethylene and alpha olefins (such as 1-butene, 1-hexene or 1-octene), and ultra low density polyethylene copolymers of ethylene and alpha olefins (such as 1-butene, 1-hexene or 1-octene). The materials for the first layers 12, 512, the second layers 14, 514, the second section 34 of the third layer 30 and the second section 334 of the third layer 330 may also include a metal foil and may be a metal foil laminate with a metal foil and a polymeric layer such as nylon. It may also be a metal foil laminate with an outer lamina of polyethylene terephthalate, a core lamina of metal foil and an inner lamina of polyethylene. In this arrangement, the polyethylene terephthalate layer serves as a protective layer to the foil, and the polyethylene layer facilitates sealing.

Specific materials that may be used for the first section 36 of the third layer 30, the first section 336 of the third layer 330 and the third section 332 of the third layer 330 include spun-bonded olefins (such as TYVEK®) and papers. Papers may include any thin, flexible materials made from a pulp from wood or other natural or synthetic fibrous materials and may be uncoated or coated with substances including, but not limited to, heat-activated adhesives.

Figure 4:
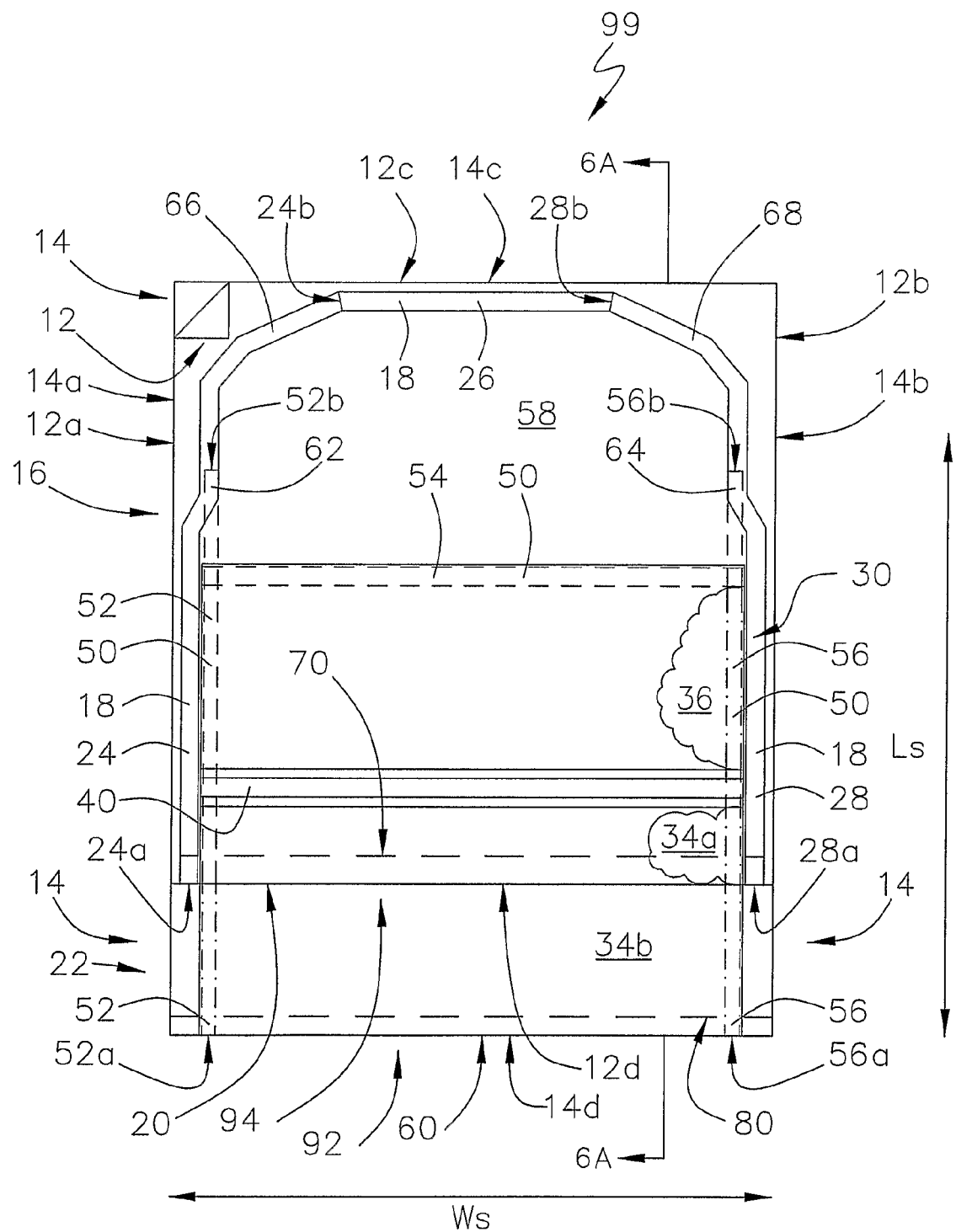
FIG. 4 is a plan view of a package comprising the first component as in FIG. 1 and the first embodiment of the second component as in FIG. 2.

Referring now to FIG. 4, a plan view with two partial cut-away sections is depicted of a package 99 comprising the component 10 of FIG. 1 and the third layer 30 of FIG. 2. FIG. 6A depicts a cross-section side view of FIG. 4, taken from the line indicated by 6A-6A in FIG. 4. As depicted in FIG. 4 and FIG. 6A, the third layer 30 is positioned between the first layer 12 and the second layer 14 so that the first section 36 is located in the pouch 16 and the second section 34 has a first portion 34a located in the pouch 16 and a second portion 34b projecting beyond the first layer bottom edge 12d. The second portion 34b of the second section 34 would be proximate the portion 22 of the second layer 14 projecting beyond the first layer bottom edge 12d if the second layer 14 has a length greater than the first layer 12.

As depicted in FIG. 4, the third layer 30 is fixed to the first layer 12 by a continuous inner peripheral seal 50 which terminates at the second layer bottom edge 14d. This inner seal 50 has a first continuous portion 52 having a first end 52a and a second end 52b, an opposing second continuous portion 56 having a first end 56a and a second end 56b and a top continuous portion 54. The third layer 30 is fixed to the second layer 14 by the first portion 52 and the second portion 56 of the inner seal 50.

The third layer 30 may, but is not required to, have a length less then the first layer 12 and the second layer 14. The third layer 30 may also, but again is not required to, have a first section 36 width less than the first layer 12 and the second layer 14.

The third layer 30 divides the pouch 16 into a first compartment 92 and a second compartment 94. The first compartment 92 is defined by the second layer 14, the third layer 30, a portion 58 of the first layer 12, the first portion 52 and the second portion 56 of the inner seal 50, and a segment of the outer seal 18 extending from a first overlap region 62 to a second overlap region 64. The first overlap region 62 is the region at which the first portion 52 of the inner seal 50 overlaps the first portion 24 of the outer seal 18. The second overlap 64 is the region at which the second portion 56 of the inner seal 50 overlaps the second portion 28 of the outer seal 18. This first compartment 92 also has a first mouth 60.

The second compartment 94 formed by the third layer 30 dividing the pouch 16 is defined by the first layer 12, the third layer 30 and the inner seal 50. The second compartment 94 has a second mouth 20.

The first end 52a of the first portion 52 and the first end 56a of the second portion 56 of the inner seal 50 are proximate the first end 24a of the first portion 24 and the first end 28a of the second portion 28 of the outer seal 18. As used herein, the term "proximate" is defined as not distant. The first ends 52a, 56a, of the first portion 52 and the second portion 56, respectively, of the inner seal 50 may, but are not required to, extend beyond the first ends 24a, 28a of the first portion 24 and the second portion 28, respectively, of the outer seal 18. The outer seal 18 fixes the first layer 12 to the second layer 14 without any interposing first section 36 of the third layer 30.

To use the package 99, an item (not shown) such as a medical device, particularly a stent for keeping open blood vessels, more particularly, an oxygen-sensitive drug-eluting stent, is placed in the first compartment 92 via the first mouth 60. A first continuous closing seal 80 is then made across the first mouth 60, sealing the second section 34 of the third layer 30 to the second layer 14. A sterilizing gas, such as ethylene oxide, is then introduced into the first compartment 92 via the breathable material of the first section 36 of the third layer 30. The sterilization process may be completed by means other than gas sterilization. These additional means included, but are not limited to, gamma radiation.

The sterilizing gas is then removed from the package 99. Removing the sterilizing gas may comprise flushing the package 99 with an inert gas and/or applying a vacuum to the package 99. The inert gas used to flush the package may be nitrogen. The nitrogen may be flushed for a time sufficient to remove the sterilizing gas. In one embodiment, a suitable flush time may be from about one second to about ten seconds at a pressure of from about 10 psi to about 30 psi, preferably for about five seconds to about ten seconds at a pressure of 30 psi. Longer flush times may be used if desired for the particular package configuration. The vacuum may be applied for a time sufficient to remove the desired quantity of gas. In one embodiment, the vacuum may be applied for from about one second to about ten seconds, preferably for from about five seconds to about ten seconds. Vacuum times may vary depending upon the package configuration, the quantity of gas to be removed, the items packaged and other variables.

Either before or after the sterilizing gas is removed from the package 99, one or more additional auxiliary items, such as a desiccant and/or scavenger, particularly an oxygen scavenger, are inserted into the second compartment 94 via the second mouth 20. Suitable desiccants include those sold by Silgel Packaging, Ltd. (Shropshire, England) under the trademark SIV-DRI™. Suitable scavengers include those sold by Mitsubishi Gas Chemical Company, Inc. (Tokyo, Japan) under the trademark PHARMAKEEP®. The first section 36 of the third layer 30 provides a breathable interface between the first compartment 92 and the second compartment 94. This allows the auxiliary item, such as the scavenging material, in the second compartment 94 to perform its functions in respect of any gas, water, etc., located in either the first compartment 92 or the second compartment 94 without coming into direct contact with the sterile contents of the first compartment 92.

A second continuous closing seal 70 is then made across the second mouth 20, sealing the second section 34 of the third layer 30 to the first layer 12 and to the second layer 14. As depicted in FIG. 4, the second closing seal 70 extends from the first peripheral side edges 12a, 14a to the opposing peripheral side edges 12b, 14b of the first layer 12 and the second layer 14. The second closing seal 70 overlaps the first portion 24 and the second portion 28 of the outer seal 18, the first portion 52 and the second portion 56 of the inner seal 50, the first layer 12, the second layer 14, and the second section 34 of the third layer 30.

As depicted in FIG. 4, the outer seal 18 comprises two layers of non-breathable material (i.e, the first layer 12 and the second layer 14). As depicted in FIG. 6B (an enlarged view of part of the view of FIG. 6A), the second closing seal 70 comprises three layers of non-breathable material (the first layer 12, the second layer 14 and the second section 34 of third layer 30). As a result, the outer seal 18 and the second closing seal 70 provide an oxygen barrier and minimize the oxygen transmission rate for the package 99. The first portion 52 and the second portion 56 of the inner seal 50 include a layer of breathable material (i.e., the first section 36 of the third layer 30). After the second closing seal 70 is formed, the first portion 52 and the second portion 56 of the inner seal 50 are substantially isolated from the external environment by oxygen barrier seals. Therefore, the contents of the first compartment 92 and the second compartment 94, particularly the first compartment 92, are protected from the environment outside the package 99; in particular, the ingress of oxygen is substantially prevented and the oxygen transmission rate is minimized. The oxygen transmission rate for the package 99 is preferably less than 0.50 cm$^3$/package/day and, more preferably, less than 0.10 cm$^3$/package/day. Oxygen transmission rate is measured in accordance with ASTM Test Method F1307-02, "Standard Test Method for Oxygen Transmission Rate Through Dry Packages Using a Coulometric Sensor" at 23° C. and 50% relative humidity using a 21% by weight concentration of oxygen gas for whole package testing.

After the second closing seal 70 is formed, the portion of the package 99 beyond the second closing seal 70 not containing any items may be removed and discarded.

Referring again to FIG. 4, a section 66 of the first portion 24 of the outer seal 18 and an opposing section 68 of the second portion 28 of the outer seal 18 may be positioned apart from the edges (e.g., 12a, 12b, 12c) of the first layer 12 and the edges (e.g., 14a, 14b, 14c) of the second layer 14 in at least one region of the package 99 by an amount sufficient to allow a user to grasp the free ends of the first layer 12 and the second layer 14 and pull apart the ends with sufficient force to open the outer seal 18. This region may be located at one or more of the corners of the package 99. This allows the user quick and easy access to the contents of the first compartment 92, for example, at the time medical personnel require the sterilized medical device. Other opening mechanisms, including, but not limited to, easy-to-peel-open package structures, tear-open notches, thumb notches and tear tapes, may be employed for the package 99 and/or for alternate embodiments of the package 99.

Figure 5:
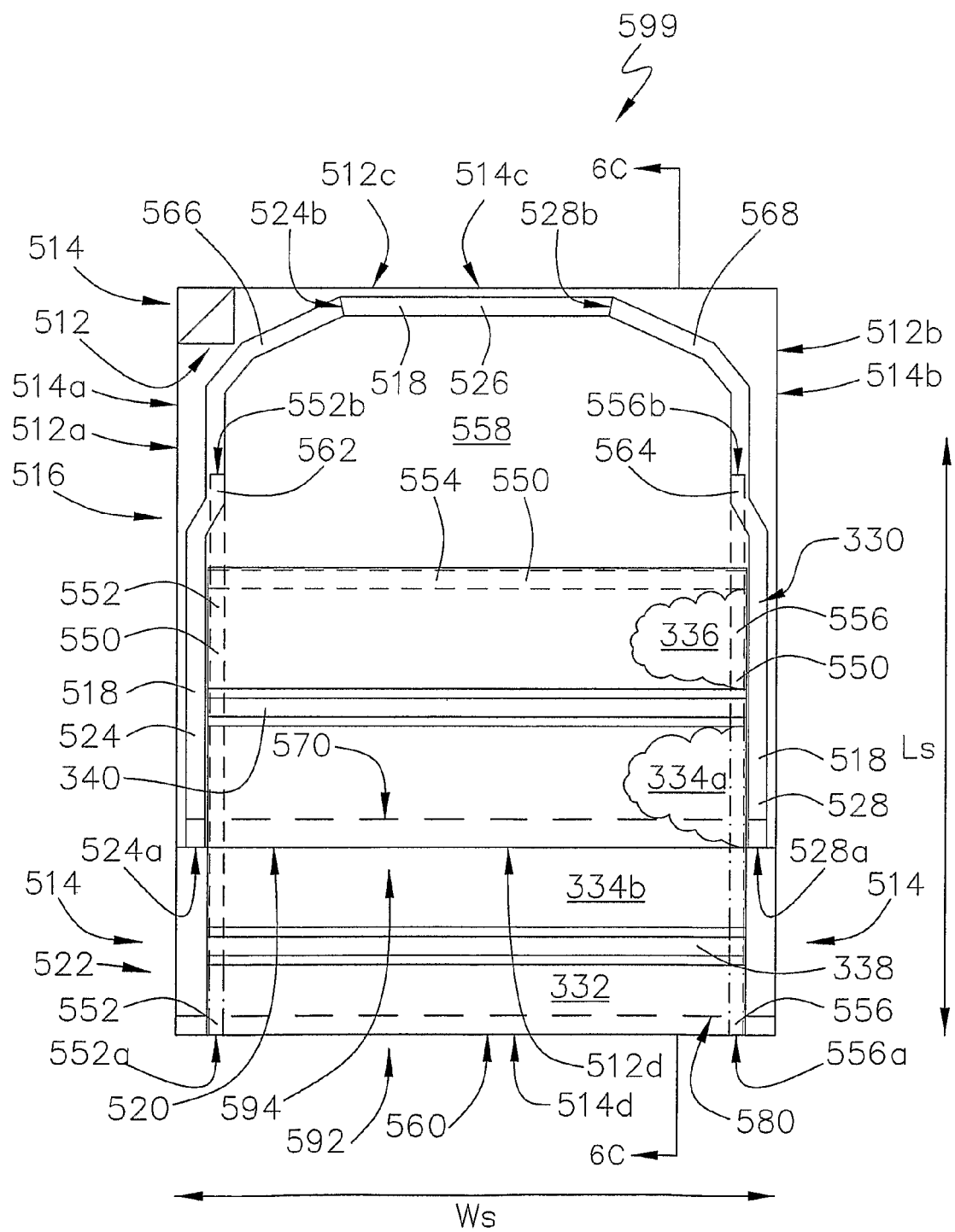
FIG. 5 is a plan view of a package comprising the first component as in FIG. 1 and the second embodiment of the second component as in FIG. 3.

Referring now to FIG. 5, a plan view with two partial cut-away sections is depicted of the preferred embodiment, the package 599 comprising the component 10 of FIG. 1 and the third layer 330 of FIG. 3. FIG. 6C depicts a cross-section side view of FIG. 5, taken from the line indicated by 6C-6C in FIG. 5. The embodiment depicted in FIG. 5 and FIG. 6C is similar to the embodiment depicted in FIG. 4 and FIG. 6A but includes the third layer 330 instead of the third layer 30. As depicted in FIG. 5 and FIG. 6C, the third layer 330 is positioned between the first layer 512 and the second layer 514. The first section 336 is located in the pouch 516. The second section 334 of the third layer 330 has a first portion 334a located in the pouch 516 and a second portion 334b projecting beyond the first layer bottom edge 512d. The third section 332 of the third layer 330 projects beyond the first layer bottom edge 512d and would be proximate the portion 522 of the second layer 514 projecting beyond the first layer bottom edge 512d if the second layer 514 has a length greater than the first layer 512.

As depicted in FIG. 5, the third layer 330 is fixed to the first layer 512 by a continuous inner peripheral seal 550 which terminates at the second layer bottom edge 514d. This inner seal 550 has a first continuous portion 552 having a first end 552a and a second end 552b, an opposing second continuous portion 556 having a first end 556a and a second end 556b and a top continuous portion 554. The third layer 330 is fixed to the second layer 514 by the first portion 552 and the second portion 556 of the inner seal 550.

The third layer 330 may, but is not required to, have a length less then the first layer 512 and the second layer 514. The third layer 330 may also, but again is not required to, have a first section 336 width less than the first layer 512 and the second layer 514.

The third layer 330 divides the pouch 516 into a first compartment 592 and a second compartment 594. The first compartment 592 is defined by the second layer 514, the third layer 330, a portion 558 of the first layer 512, the first portion 552 and the second portion 556 of the inner seal 550, and a segment of the outer seal 518 extending from a first overlap region 562 to a second overlap region 564. The first overlap region 562 is the region at which the first portion 552 of the inner seal 550 overlaps the first portion 524 of the outer seal 518. The second overlap 564 is the region at which the second portion 556 of the inner seal 550 overlaps the second portion 528 of the outer seal 518. This first compartment 592 also has a first mouth 560.

The second compartment 594 formed by the third layer 330 dividing the pouch 516 is defined by the first layer 512, the third layer 530 and the inner seal 550. The second compartment 594 has a second mouth 520.

The first end 552a of the first portion 552 and the first end 556a of the second portion 556 of the inner seal 550 are proximate the first end 524a of the first portion 524 and first end 528a of the second portion 528 of the outer seal 518. The first ends 552a, 556a of the first portion 552 and the second portion 556, respectively, of the inner seal 550 may, but are not required to, extend beyond the first ends 524a, 528a of the first portion 524 and the second portion 528, respectively, of the outer seal 518. The outer seal 518 fixes the first layer 512 to the second layer 514 without any interposing first section 336 of the third layer 330.

To use the package 599, an item (not shown) such as a medical device, is placed in the first compartment 592 via the first mouth 560. A first continuous closing seal 580 is then made across the first mouth 560, sealing the third section 332 of the third layer 330 to the second layer 514. A sterilizing gas, such as ethylene oxide, is then introduced into the first compartment 592 via the breathable material of the first section 336 and the breathable material of the third section 332 of the third layer 330. The sterilizing gas is then removed from the package 599. Removing the sterilizing gas may comprise flushing the package 599 with an inert gas and applying a vacuum to the package 599. Either before or after the sterilizing gas is removed from the package 599, one or more additional auxiliary items, such as a desiccant and/or scavenger, particularly an oxygen scavenger, are inserted into the second compartment 594 via the second mouth 520. The first section 336 of the third layer 330 provides a breathable interface between the first compartment 592 and the second compartment 594. This allows the auxiliary item, such as the scavenging material, in the second compartment 594 to perform its functions in respect of any gas, water, etc., located in either the first compartment 592 or the second compartment 594 without coming into direct contact with the sterile contents of the first compartment 592.

A second continuous closing seal 570 is then made across the second mouth 520, sealing the second section 334 of the third layer 330 to the first layer 512 and to the second layer 514. As depicted in FIG. 5, the second closing seal 570 extends from the first peripheral side edges 512a, 514a to the opposing peripheral side edges 512b, 514b of the first layer 512 and the second layer 514. The second closing seal 570 overlaps the first portion 524 and the second portion 528 of the outer seal 518, the first portion 552 and the second portion 556 of the inner seal 550, the first layer 512, the second layer 514, and the second section 334 of the third layer 330.

As depicted in FIG. 5, the outer seal 518 comprises two layers of non-breathable material (i.e, the first layer 512 and the second layer 514). As depicted in FIG. 6D (an enlarged view of part of the view of FIG. 6C), the second closing seal 570 comprises three layers of non-breathable material (the first layer 512, the second layer 514 and the second section 334 of third layer 330). As a result, the outer seal 518 and the second closing seal 570 provide an oxygen barrier and minimize the oxygen transmission rate for the package 599. The first portion 552 and the second portion 556 of the inner seal 550 include a layer of breathable material (i.e., the first section 336 of the third layer 330). After the second closing seal 570 is formed, the first portion 552 and the second portion 556 of the inner seal 550 are substantially isolated from the external environment by oxygen barrier seals. Therefore, the contents of the first compartment 592 and the second compartment 594, particularly the first compartment 592, are protected from the environment outside the package 599; in particular, the ingress of oxygen is substantially prevented and the oxygen transmission rate is minimized. The oxygen transmission rate for the package 599 is preferably less than 0.50 cm$^3$/package/day and, more preferably, less than 0.10 cm$^3$/package/day.

After the second closing seal 570 is formed, the portion of the package 599 beyond the second closing seal 570 not containing any items may be removed and discarded.

Referring again to FIG. 5, a section 566 of the first portion 524 of the outer seal 518 and an opposing section 568 of the second portion 528 of the outer seal 518 may be positioned apart from the edges (e.g., 512a, 512b, 512c) of the first layer 512 and the edges (e.g., 514a, 514b, 514c) of the second layer 514 in at least one region of the package 599 by an amount sufficient to allow a user to grasp the free ends of the first layer 512 and the second layer 514 and pull apart the ends with sufficient force to open the outer seal 518. This region may be located at one or more of the corners of the package 599. This allows the user quick and easy access to the contents of the first compartment 592. Other opening mechanisms, including, but not limited to, easy-to-peel-open package structures, tear-open notches, thumb notches and tear tapes, may be employed for the package 599 and/or for alternate embodiments of the package 599.

All the various seals included in the packages 99, 599, including, but not limited to, the outer seals, the inner seals, the overlap seals and the closing seals, may be formed by various methods, including, but not limited to, heat seal, weld seal, ultrasonic seal or adhesive seal. For example, heat seals may be formed via a hot bar sealer. In using a hot bar sealer, adjacent polymeric layers of the packages 99, 599 are held together by opposing sealer bars of which at least one is heated to cause the adjacent polymeric layers to fusion bond by application of heat and pressure across the area to be sealed. Although specific seal conditions will vary depending upon the thickness, package materials used, package configuration, sealing equipment and other variables, a suitable seal using typical equipment known in the art may be achieved with a seal time from about one second to about ten seconds using an upper bar seal temperature of from about 110° C. to about 250° C. and a lower bar seal temperature of from about 20° C. to about 100° C. and with a seal pressure of from about 30 psi to about 150 psi. In one preferred embodiment, a seal time of about five seconds with an upper jaw seal temperature of about 150° C. and a lower jaw seal temperature of about 60° C. and with a seal pressure of about 40 psi may be employed. Seals may also be formed via an impulse seal. An impulse seal is formed via application of heat and pressure using opposing bars similar to that of the hot bar sealer except that at least one of the bars has a covered wire or ribbon through which electric current is passed for a brief time period to cause the adjacent layers to fusion bond.

The first layers 12, 512, the second layers 14, 514 and/or the third layers 30, 330 of the packages 99, 599 may be printed with indicia or affixed with indicia-printed labels to identify the package contents and/or provide the user additional information regarding the contents.

Additionally, the packages 99, 599 may be particularly designed to allow for convenient storage of the packages 99, 599 and their contents. As one non-limiting example, the top edges 12c, 512c, 14c, 514c of the first layers 12, 512 and the second layers 14, 514 may be extended past the top portions 26, 526 of the outer seal 18, 518 to allow for a supplemental area in which a hanging hole may be placed.

One skilled in the art will conceive many modifications and other embodiments of the present invention from the benefit of the teachings disclosed herein. The invention and several embodiments were also disclosed and described in Irish Patent Application S2004/0826 filed Dec. 8, 2004. It is to be understood that the present invention includes the embodiments disclosed above but is not limited to the specific embodiments disclosed and that modifications and other embodiments will be apparent to those skilled the art from the disclosure and these modifications and embodiments are intended to be included within the scope of the claims.

What is claimed is:

1. A package comprising:
   a first layer comprising non-breathable polymeric material;
   a second layer comprising non-breathable polymeric material;
   a third layer comprising a first section comprising breathable polymeric material and a second section comprising non-breathable polymeric material;
   wherein the first layer has a perimeter having a first peripheral side edge, an opposing second peripheral side edge, a peripheral top edge and an opposing peripheral bottom edge;
   wherein the second layer has a perimeter having a first peripheral side edge, an opposing second peripheral side edge, a peripheral top edge and an opposing peripheral bottom edge;
   wherein the first and second layers are fixed together by a continuous outer peripheral seal having a first continuous portion extending from a first end of the first portion to a second end thereof, an opposing second continuous portion extending from a first end of the second portion to a second end thereof and a top continuous portion extending from the second end of the first portion to the second end of the second portion thereby defining a non-breathable pouch having an opening formed by the first and second layer bottom edges and the first ends of the first and second portions of the outer seal;
   wherein the third layer is positioned between the first and second layers;
   wherein the third layer is fixed to the first layer by a continuous inner peripheral seal having a first continuous portion extending from a first end of the first portion to a second end thereof, an opposing second continuous portion extending from a first end of the second portion to a second end thereof and a top continuous portion extending from the second end of the first portion to the second end of the second portion;
   wherein the third layer is fixed to the second layer by the first and second portions of the inner seal;
   wherein the inner seal has a first seal end and an opposing second seal end wherein the first seal end is proximate the first end of the first portion of the outer seal end and the second seal end is proximate the first end of the second portion of the outer seal;
   wherein the outer seal fixes the first layer to the second layer without any interposing first section of the third layer;
   wherein the opening formed by the first and second layers is divided by the third layer to form a first mouth between the second and third layers and a second mouth between the first and third layers, such that
   a first compartment of the pouch is defined by (i) the second layer, (ii) the third layer, (iii) a continuous sealed edge between the second and third layers formed by the first portion of the inner seal, the second portion of the inner seal and a segment of the outer seal having a first end proximate the second end of the first portion of the inner seal and a second end proximate the second end of the second portion of the inner seal and (iv) the first mouth; and
   a second compartment of the pouch is defined by (i) the first layer, (ii) the third layer, (iii) the inner seal between the first and third layers and (iv) the second mouth.

2. A package according to claim 1 wherein the package is flexible.

3. A package according to claim 1 wherein the second layer has a length greater than the first layer.

4. A package according to claim 1 wherein the first layer has a length greater than the second layer.

5. A package according to claim 1 wherein the third layer has a length less than the first and second layers.

6. A package according to claim 1 wherein the third layer has a first section width less than the first and second layers.

7. A package according to claim 1 wherein the second and third layers are adapted to fix together and form a first continuous closing seal across the first mouth.

8. A package according to claim 1 wherein the first and third layers are adapted to fix together and form a second continuous closing seal across the second mouth.

9. A package according to claim 8 wherein the second closing seal comprises a section of the second section of the third layer.

10. A package according to claim 9 wherein the second closing seal forms a sealed package having an oxygen transmission rate from 0 to about 0.50 $cm^3$/package/day as measured in accordance with ASTM F1307-02 at 23° C. and 50% relative humidity and using a 21% by weight concentration of oxygen gas.

11. A package according to claim 10 wherein the oxygen transmission rate is from 0 to about 0.10 $cm^3$/package/day as measured in accordance with ASTM F1307-02 at 23° C. and 50% relative humidity and using a 21% by weight concentration of oxygen gas.

12. A package according to claim 1 wherein the third layer further comprises a third section comprising a breathable polymeric material wherein the second section is positioned between and connects the first and third sections.

13. A package according to claim 1 wherein the first and second layers and the second section of the third layer have a Gurley Hill porosity value greater than 100 seconds per 100 $cm^3$ of air as measured in accordance with ISO 5636-5.

14. A package according to claim 1 wherein the non-breathable material of the first and second layers and the second section of the third layer comprises heat sealable polymer.

15. A package according to claim 14 wherein the heat sealable polymer comprises polyolefin, polyethylene terephthalate, nylon, or ethylene homopolymer or copolymer.

16. A package according to claim 15 wherein the heat sealable polymer is polyethylene.

17. A package according to claim 1 wherein the non-breathable material of the first and second layers and the second section of the third layer comprises metal foil.

18. A package according to claim 1 wherein the non-breathable material of the first and second layers and the second section of the third layer comprises metal foil laminate comprising polyethylene terephthalate, metal foil and polyethylene.

19. A package according to claim 1 wherein the non-breathable material of the first and second layers and the second section of the third layer comprises metal foil laminate comprising metal foil and nylon.

20. A package according to claim 1 wherein the first section of the third layer has a Gurley Hill porosity value from 0 to 100 seconds per 100 $cm^3$ of air as measured in accordance with ISO 5636-5.

21. A package according to claim 12 wherein the first and third sections of the third layer have a Gurley Hill porosity value from 0 to 100 seconds per 100 cm$^3$ of air as measured in accordance with ISO 5636-5.

22. A package according to claim 1 wherein the breathable material of the first section of the third layer comprises spun-bonded olefin or paper.

23. A package according to claim 12 wherein the breathable material of the first and third sections of the third layer comprises spun-bonded olefin or paper.

24. A package comprising:
a sheet comprising non-breathable polymeric material wherein the sheet has a folded edge forming a first layer and a second layer;
a third layer comprising a first section comprising breathable polymeric material and a second section comprising non-breathable polymeric material;
wherein the first layer has a perimeter having a first peripheral side edge, an opposing second peripheral side edge, a peripheral top edge and an opposing peripheral bottom edge;
wherein the second layer has a perimeter having a first peripheral side edge, an opposing second peripheral side edge, a peripheral top edge and an opposing peripheral bottom edge;
wherein the first and second layers are fixed together by an outer peripheral seal having a first continuous portion extending from a first end of the first portion to a second end thereof and an opposing second continuous portion extending from a first end of the second portion to a second end thereof wherein the second ends of the first and second portion are contiguous the folded edge of the sheet forming the first and second layers thereby defining a non-breathable pouch having an opening formed by the first and second layer bottom edges and the first ends of the first and second portions of the outer seal;
wherein the third layer is positioned between the first and second layers;
wherein the third layer is fixed to the first layer by a continuous inner peripheral seal having a first continuous portion extending from a first end of the first portion to a second end thereof, an opposing second continuous portion extending from a first end of the second portion to a second end thereof and a top continuous portion extending from the second end of the first portion to the second end of the second portion;
wherein the third layer is fixed to the second layer by the first and second portions of the inner seal;
wherein the inner seal has a first seal end and an opposing second seal end wherein the first seal end is proximate the first end of the first portion of the outer seal and the second seal end is proximate the first end of the second portion of the outer seal;
wherein the first and second portions of the outer seal fix the first layer to the second layer without any interposing first section of the third layer;
wherein the opening formed by the first and second layers is divided by the third layer to form a first mouth between the second and third layers and a second mouth between the first and third layers, such that
a first compartment of the pouch is defined by (i) the second layer, (ii) the third layer, (iii) the folded edge of the sheet forming the first and second layers, (iii) a first sealed edge between the second and third layers formed by the first portion of the inner seal and a segment of the first portion of the outer seal having a first end proximate the second end of the first continuous portion of the inner seal and a second end proximate the second end of the first portion of the outer seal, iv) an opposing second sealed edge between the second and third layers formed by the second portion of the inner seal and a segment of the second portion of the outer seal having a first end proximate the second end of the second portion of the inner seal and a second end proximate the second end of the second portion of the outer seal and (iv) the first mouth; and
a second compartment of the pouch is defined by (i) the first layer, (ii) the third layer, (iii) the inner seal between the first and third layers and (iv) the second mouth.

25. A package according to claim 24 wherein the third layer has a first section width less than the first and second layers.

26. A package according to claim 24 wherein the first and third layers are adapted to fix together and form a continuous closing seal across the second mouth wherein the closing seal comprises a section of the second section of the third layer and forms a sealed package having an oxygen transmission rate from 0 to about 0.50 cm$^3$/package/day, preferably 0 to about 0.10 cm$^3$/package/day, as measured in accordance with ASTM F1307-02 at 23° C. and 50% relative humidity and using a 21% by weight concentration of oxygen gas.

27. A package according to claim 24 wherein the third layer further comprises a third section comprising a breathable polymeric material wherein the second section is positioned between and connects the first and third sections.

28. A package according to claim 24 wherein the first and second layers and the second section of the third layer have a Gurley Hill porosity value greater than 100 seconds per 100 cm$^3$ of air as measured in accordance with ISO 5636-5 and the first section of the third layer has a Gurley Hill porosity value from 0 to 100 seconds per 100 cm$^3$ of air as measured in accordance with ISO 5636-5.

29. A package according to claim 27 wherein the first and second layers and the second section of the third layer have a Gurley Hill porosity value greater than 100 seconds per 100 cm$^3$ of air as measured in accordance with ISO 5636-5 and the first and third sections of the third layer have a Gurley Hill porosity value from 0 to 100 seconds per 100 cm$^3$ of air as measured in accordance with ISO 5636-5.

30. A flexible package comprising
a first layer comprising non-breathable polymeric material;
a second layer comprising non-breathable polymeric material;
a third layer comprising a first section comprising breathable polymeric material, a second section comprising non-breathable polymeric material and a third section comprising breathable polymeric material, wherein the second section is positioned between and connects the first and third sections;
wherein the first layer has a perimeter having a first peripheral side edge, an opposing second peripheral side edge, a peripheral top edge and an opposing peripheral bottom edge;
wherein the second layer has a perimeter having a first peripheral side edge, an opposing second peripheral side edge, a peripheral top edge and an opposing peripheral bottom edge;
wherein the first and second layers are fixed together by a continuous outer peripheral seal having a first continuous portion extending from a first end of the first portion to a second end thereof, an opposing second continuous portion extending from a first end of the second portion to a second end thereof and a top continuous portion extending from the second end of the first portion to the second end of the second portion thereby defining a non-breathable pouch having an opening formed by the first and second layer bottom edges and the first ends of the first and second portions of the outer seal;

wherein the second layer has a length greater than the first layer with a portion projecting beyond the first layer bottom edge;

wherein the third layer has a length less than the first and second layers and is positioned between the first and second layers;

wherein the third layer is fixed to the first layer by a continuous inner peripheral seal having a first continuous portion extending from a first end of the first portion to a second end thereof, an opposing second continuous portion extending from a first end of the second portion to a second end thereof and a top continuous portion extending from the second end of the first portion to the second end of the second portion;

wherein the third layer is fixed to the second layer by the first and second portions of the inner seal;

wherein the inner seal has a first seal end and an opposing second seal end wherein the first seal end is proximate the first end of the first portion of the outer seal and the second seal end is proximate the first end of the second portion of the outer seal;

wherein the first section of the third layer is located in the pouch defined by the first and second layers, the second section of the third layer has a first portion projecting beyond the first layer bottom edge and a second portion located in the pouch and the third section of the third layer projects beyond the first layer bottom edge and is proximate the portion of the second layer projecting beyond the first layer bottom edge;

wherein the outer seal fixes the first layer to the second layer without any interposing first section of the third layer;

wherein the opening formed by the first and second layers is divided by the third layer to form a first mouth between the second and third layers and a second mouth between the first and third layers, such that a first compartment of the pouch is defined by (i) the second layer, (ii) the third layer, (iii) a continuous sealed edge between the second and third layers formed by the first portion of the inner seal, the second portion of the inner seal and a segment of the outer seal having a first end proximate the second end of the first portion of the inner seal and a second end proximate the second end of the second portion of the inner seal and (iv) the first mouth; and a second compartment of the pouch is defined by (i) the first layer, (ii) the third layer, (iii) the inner seal between the first and third layers and (iv) the second mouth.

31. A flexible package according to claim 30 wherein the third layer has a first section width less than the first and second layers.

32. A flexible package comprising
a first layer comprising non-breathable polymeric material;
a second layer comprising non-breathable polymeric material;
a third layer comprising a first section comprising breathable polymeric material, a second section comprising non-breathable polymeric material and a third section comprising breathable polymeric material, wherein the second section is positioned between and connects the first and third sections;

wherein the first and second layers and the second section of the third layer have a Gurley Hill porosity value greater than 100 seconds per 100 cm$^3$ of air as measured in accordance with ISO 5636-5;

wherein the first and third sections of the third layer have a Gurley Hill porosity value from 0 to 100 seconds per 100 cm$^3$ of air as measured in accordance with ISO 5636-5;

wherein the first layer has a perimeter having a first peripheral side edge, an opposing second peripheral side edge, a peripheral top edge and an opposing peripheral bottom edge;

wherein the second layer has a perimeter having a first peripheral side edge, an opposing second peripheral side edge, a peripheral top edge and an opposing peripheral bottom edge;

wherein the first and second layers are fixed together by a continuous outer peripheral seal having a first continuous portion extending from a first end of the first portion to a second end thereof, an opposing second continuous portion extending from a first end of the second portion to a second end thereof and a top continuous portion extending from the second end of the first portion to the second end of the second portion thereby defining a non-breathable pouch having an opening formed by the first and second layer bottom edges and the first ends of the first and second portions of the outer seal;

wherein the second layer has a length greater than the first layer with a portion projecting beyond the first layer bottom edge;

wherein the third layer has a length less than the first and second layers and is positioned between the first and second layers;

wherein the third layer is fixed to the first layer by a continuous inner peripheral seal having a first continuous portion extending from a first end of the first portion to a second end thereof, an opposing second continuous portion extending from a first end of the second portion to a second end thereof and a top continuous portion extending from the second end of the first portion to the second end of the second portion;

wherein the third layer is fixed to the second layer by the first and second continuous portions of the inner seal;

wherein the inner seal has a first seal end and an opposing second seal end wherein the first seal end is proximate the first end of the first portion of the outer seal and the second seal end is proximate the first end of the second portion of the outer seal;

wherein the first section of the third layer is located in the pouch defined by the first and second layers, the second section of the third layer has a first portion projecting beyond the first layer bottom edge and a second portion located in the pouch and the third section of the third layer projects beyond the first layer bottom edge and is proximate the portion of the second layer projecting beyond the first layer bottom edge;

wherein the outer seal fixes the first layer to the second layer without any interposing first section of the third layer;

wherein the opening formed by the first and second layers is divided by the third layer to form a first mouth between the second and third layers and a second mouth between the first and third layers, such that a first, compartment of the pouch is defined by (i) the second layer, (ii) the third layer, (iii) a continuous sealed edge between the second and third layers formed by the first portion of the inner seal, the second portion of the inner seal and a segment of the outer seal having a first end proximate the second end of the first portion of the inner seal and a second end proximate the second end of the second portion of the inner seal and (iv) the first mouth; and a second compartment of the pouch is defined by (i) the first layer, (ii) the third layer, (iii) the inner seal between the first and third layers and (iv) the second mouth.

33. A flexible package according to claim 32 wherein the third layer has a first section width less than the first and second layers.

34. A flexible package comprising
a first layer comprising metal foil laminate comprising an outer lamina of polyethylene terephthalate, a core lamina of metal foil and an inner lamina of polyethylene;
a second layer comprising metal foil laminate comprising an outer lamina of polyethylene terephthalate, a core lamina of metal foil and an inner lamina of polyethylene;
a third layer comprising a first section comprising spun-bonded olefin, a second section comprising polyethylene and a third section comprising spun-bonded olefin;
wherein the first layer has a perimeter having a first peripheral side edge, an opposing second peripheral side edge, a peripheral top edge and an opposing peripheral bottom edge;
wherein the second layer has a perimeter having a first peripheral side edge, an opposing second peripheral side edge, a peripheral top edge and an opposing peripheral bottom edge;
wherein the first and second layers are fixed together by a continuous outer peripheral seal having a first continuous portion extending from a first end of the first portion to a second end thereof, an opposing second continuous portion extending from a first end of the second portion to a second end thereof and a top continuous portion extending from the second end of the first portion to the second end of the second portion thereby defining a non-breathable pouch having an opening formed by the first and second layer bottom edges and the first ends of the first and second portions of the outer seal;
wherein the second layer has a length greater than the first layer and a portion projecting beyond the first layer bottom edge;
wherein the third layer has a length less than the first and second layers and is positioned between the first and second layers;
wherein the third layer is fixed to the first layer by a continuous inner peripheral seal having a first continuous portion extending from a first end of the first portion to a second end thereof, an opposing second continuous portion extending from a first end of the second portion to a second end thereof and a top continuous portion extending from the second end of the first portion to the second end of the second portion;
wherein the third layer is fixed to the second layer by the first and second portions of the inner seal;
wherein the inner seal has a first seal end and an opposing second seal end wherein the first seal end is proximate the first end of the first portion of the outer seal and the second seal end is proximate the first end of the second portion of the outer seal;
wherein the first section of the third layer is located in the pouch defined by the first and second layers, the second section of the third layer has a first portion projecting beyond the first layer bottom edge and a second portion located in the pouch and the third section of the third layer projects beyond the first layer bottom edge and is proximate the portion of the second layer projecting beyond the first layer bottom edge;
wherein the outer seal fixes the first layer to the second layer without any interposing first section of the third layer;
wherein the opening formed by the first and second layers is divided by the third layer to form a first mouth between the second and third layers and a second mouth between the first and third layers, such that a first compartment of the pouch is defined by (i) the second layer, (ii) the third layer, (iii) a continuous sealed edge between the second and third layers formed by the first portion of the inner seal, the second portion of the inner seal and a segment of the outer seal having a first end proximate the second end of the first portion of the inner seal and a second end proximate the second end of the second portion of the inner seal and (iv) the first mouth; and a second compartment of the pouch is defined by (i) the first layer, (ii) the third layer, (iii) the inner seal between the first and third layers and (iv) the second mouth.

35. A flexible package according to claim 34 wherein the third layer has a first section width less than the first and second layers.

36. A method of packaging an item comprising: providing a package comprising:
a first layer comprising non-breathable polymeric material;
a second layer comprising non-breathable polymeric material;
a third layer comprising a first section comprising breathable polymeric material and a second section comprising non-breathable polymeric material;
wherein the first layer has a perimeter having a first peripheral side edge, an opposing second peripheral side edge, a peripheral top edge and an opposing peripheral bottom edge;
wherein the second layer has a perimeter having a first peripheral side edge, an opposing second peripheral side edge, a peripheral top edge and an opposing peripheral bottom edge;
wherein the first and second layers are fixed together by a continuous outer peripheral seal having a first continuous portion extending from a first end of the first portion to a second end thereof, an opposing second continuous portion extending from a first end of the second portion to a second end thereof and a top continuous portion extending from the second end of the first portion to the second end of the second portion thereby defining a non-breathable pouch having an opening formed by the first and second layer bottom edges and the first ends of the first and second portions of the outer seal;
wherein the third layer is positioned between the first and second layers;
wherein the third layer is fixed to the first layer by a continuous inner peripheral seal having a first continuous portion extending from a first end of the first portion to a second end thereof, an opposing second continuous portion extending from a first end of the second portion to a second end thereof and a top continuous portion extending from the second end of the first portion to the second end of the second portion;

wherein the third layer is fixed to the second layer by the first and second portions of the inner seal;

wherein the inner seal has a first seal end and an opposing second seal end wherein the first seal end is proximate the first end of the first portion of the outer seal end and the second seal end is proximate the first end of the second portion of the outer seal;

wherein the outer seal fixes the first layer to the second layer without any interposing first section of the third layer;

wherein the opening formed by the first and second layers is divided by the third layer to form a first mouth between the second and third layers and a second mouth between the first and third layers, such that a first compartment of the pouch is defined by (i) the second layer, (ii) the third layer, (iii) a continuous sealed edge between the second and third layers formed by the first portion of the inner seal, the second portion of the inner seal and a segment of the outer seal having a first end proximate the second end of the first portion of the inner seal and a second end proximate the second end of the second portion of the inner seal and (iv) the first mouth; and a second compartment of the pouch is defined by (i) the first layer, (ii) the third layer, (iii) the inner seal between the first and third layers and (iv) the second mouth;

placing a first item in the first compartment;

closing the first compartment by forming a first continuous closing seal across the first mouth;

introducing a sterilizing gas into the first compartment through the first section of the third layer;

removing the sterilizing gas from the package;

placing a second item in the second compartment;

closing the second compartment by forming a second continuous closing seal across the second mouth.

37. A method according to claim 36 wherein the first item comprises a medical device.

38. A method according to claim 36 wherein the sterilizing gas comprises ethylene oxide.

39. A method according to claim 36 wherein the second item comprises a scavenger, a desiccant or a combination thereof.

40. A method according to claim 39 wherein the scavenger comprises an oxygen scavenger.

41. A method according to claim 36 wherein removing the sterilizing gas comprises flushing the package with an inert gas and applying a vacuum to the package.

42. A method according to claim 41 wherein the inert gas used to flush the package is nitrogen which is flushed for about at least five seconds at a pressure of about 30 psi.

43. A method according to claim 41 wherein the vacuum is applied for about at least five seconds.

44. A method according to claim 36 wherein forming the first and second closing seals comprises heat sealing, weld sealing, ultrasonic sealing, adhesive sealing or a combination thereof.

45. A method according to claim 44 wherein heat sealing comprises clamping the first and second mouth between upper and lower jaws of a sealing device, with a seal time of about at least five seconds, with an upper jaw seal temperature of about at least 150° C. and a lower jaw seal temperature of about at least 60° C. and with a seal pressure of about at least 40 psi.

46. A method according to claim 36 wherein the second closing seal comprises a section of the second section of the third layer.

47. A method according to claim 46 wherein the second closing seal forms a sealed package having an oxygen transmission rate from 0 to about 0.50 $cm^3$/package/day as measured in accordance with ASTM F1307-02 at 23° C. and 50% relative humidity and using a 21% by weight concentration of oxygen gas.

48. A method according to claim 47 wherein the oxygen transmission rate is from 0 to 0.10 $cm^3$/package/day as measured in accordance with ASTM F1307-02 at 23° C. and 50% relative humidity and using a 21% by weight concentration of oxygen gas.

49. A method according to claim 36 wherein the package is flexible.

50. A method according to claim 36 wherein the second layer has a length greater than the first layer.

51. A method according to claim 36 wherein the third layer has a length less than the first and second layers.

52. A method according to claim 36 wherein the third layer has a first section width less than the first and second layers.

53. A method according to claim 36 wherein the third layer further comprises a third section comprising a breathable polymeric material wherein the second section is positioned between and connects the first and third sections.

54. A method according to claim 36 wherein the first and second layers and the second section of the third layer have a Gurley Hill porosity value greater than 100 seconds per 100 $cm^3$ of air as measured in accordance with ISO 5636-5.

55. A method according to claim 36 wherein the non-breathable material of the first and second layers and the second section of the third layer comprises heat sealable polymer.

56. A method according to claim 55 wherein the heat sealable polymer comprises polyolefin, polyethylene terephthalate, nylon, or ethylene homopolymer or copolymer.

57. A method according to claim 56 wherein the heat sealable polymer is polyethylene.

58. A method according to claim 36 wherein the non-breathable material of the first and second layers and the second section of the third layer comprises metal foil.

59. A method according to claim 36 wherein the non-breathable material of the first and second layers and the second section of the third layer comprises metal foil laminate comprising polyethylene terephthalate, metal foil and polyethylene.

60. A method according to claim 36 wherein the non-breathable material of the first and second layers and the second section of the third layer comprises metal foil laminate comprising metal foil and nylon.

61. A method according to claim 36 wherein the first section of the third layer has a Gurley Hill porosity value from 0 to 100 seconds per 100 cm$^3$ of air as measured in accordance with ISO 5636-5.

62. A method according to claim 53 wherein the first and third sections of the third layer have a Gurley Hill porosity value from 0 to 100 seconds per 100 cm$^3$ of air as measured in accordance with ISO 5636-5.

63. A method according to claim 36 wherein the breathable material of the first section of the third layer comprises spun-bonded olefin or paper.

64. A method according to claim 53 wherein the breathable material of the first and third sections of the third layer comprises spun-bonded olefin or paper.

* * * * *

UNITED STATES PATENT AND TRADEMARK OFFICE
CERTIFICATE OF CORRECTION

| | | |
|---|---|---|
| PATENT NO. | : 7,938,580 B2 | Page 1 of 1 |
| APPLICATION NO. | : 11/667719 | |
| DATED | : May 10, 2011 | |
| INVENTOR(S) | : Paul Gaskell et al. | |

It is certified that error appears in the above-identified patent and that said Letters Patent is hereby corrected as shown below:

On the Title page, in item (22), in column 1, in "PCT Filed", line 2, delete "(Under 37 CFR 1.47)".

On the Title page, in item (86), in column 1, in "PCT No.", line 4, insert -- (Under 37 CFR 1.47) -- underneath Mar. 24, 2008.

In the Specification

In column 2, line 50, delete "package" and insert -- package. --.

In column 4, line 33, delete "material" and insert -- material. --.

In column 6, line 14, delete "then" and insert -- than --.

In column 8, line 44, delete "then" and insert -- than --.

In the Claims

In column 17, line 4, in claim 32, delete "first," and insert -- first --.

Signed and Sealed this
First Day of March, 2016

Michelle K. Lee
*Director of the United States Patent and Trademark Office*